United States Patent
Davies

(10) Patent No.: US 11,173,142 B2
(45) Date of Patent: Nov. 16, 2021

(54) CANCER TREATMENT COMPOSITION

(71) Applicant: BOTANICAL RESOURCE HOLDINGS (PROPRIETARY) LIMITED, Somerset West (ZA)

(72) Inventor: Richard Paul Davies, Somerset West (ZA)

(73) Assignee: Botanical Resource Holdings (Proprietary) Limited, Somerset West (ZA)

( * ) Notice: Subject to any disclaimer, the term of this patent is extended or adjusted under 35 U.S.C. 154(b) by 180 days.

(21) Appl. No.: 15/562,069

(22) PCT Filed: Mar. 24, 2016

(86) PCT No.: PCT/IB2016/051675
§ 371 (c)(1),
(2) Date: Sep. 27, 2017

(87) PCT Pub. No.: WO2016/157045
PCT Pub. Date: Oct. 6, 2016

(65) Prior Publication Data
US 2018/0064685 A1 Mar. 8, 2018

(30) Foreign Application Priority Data
Mar. 27, 2015 (ZA) .................. 2015/02137

(51) Int. Cl.
*A61K 31/404* (2006.01)
*A61K 9/02* (2006.01)
*A61K 36/185* (2006.01)
*A61K 9/48* (2006.01)

(52) U.S. Cl.
CPC .............. *A61K 31/404* (2013.01); *A61K 9/02* (2013.01); *A61K 9/4866* (2013.01); *A61K 36/185* (2013.01)

(58) Field of Classification Search
None
See application file for complete search history.

(56) References Cited

U.S. PATENT DOCUMENTS 6,288,104 B1 * 9/2001 Gericke ............... A61K 31/404
514/421

FOREIGN PATENT DOCUMENTS

| WO | 9746234 A1 | 12/1997 |
| WO | 2010106495 A1 | 9/2010 |
| WO | 2014155351 A1 | 10/2014 |

OTHER PUBLICATIONS

Patnala (Journal of Ethnopharmacology (2009), vol. 121, pp. 86-91).*
Patnala (J Pharm Pharmaceutical Sci (2010), vol. 13, No. 4, pp. 558-570).*

* cited by examiner

*Primary Examiner* — Susan Hoffman
(74) *Attorney, Agent, or Firm* — W&C IP

(57) ABSTRACT

The present invention relates to anti-cancer compositions based on extracts of a plant from the Mesembryanthemaceae family, in particular *Mesembryanthemum tortuosum* (*Sceletium tortuosum*), their use in the treatment of cancer, and methods of manufacturing the compositions. The anti-cancer compositions of the present invention include Δ7 mesembrenone.

13 Claims, 4 Drawing Sheets

CANCER TREATMENT COMPOSITION

BACKGROUND OF THE INVENTION

This invention relates to anti-cancer compositions based on extracts of a plant from the Mesembryanthemaceae family, in particular *Mesembryanthemum tortuosum* (*Sceletium tortuosum*), their use in the treatment of cancer, and methods of manufacturing the compositions.

*Mesembryanthemum tortuosum*, or *Sceletium tortuosum* as it is more commonly referred to in modern times, has been used for many centuries by indigenous peoples of Southern Africa, most notably the southern parts of the Western Cape and Namaqualand, and its use has been recorded in the literature for over 300 years. When prepared for chewing, typically by crushing of selected parts of the plant material, fermentation and drying, the resultant product, known locally as "kougoed" (stuff to chew), "Channa" or "Kanna", is said to have mood enhancing and stimulant properties, and even pain and hunger relieving properties.

US patent publication 2012/0004275 discloses compositions including as active ingredient an extract of a plant of the family Mesembryanthemaceae with mesembrenol and mesembrenone as the two major alkaloids present and to their use as PDE4 inhibitors.

SUMMARY OF THE INVENTION

According to a first aspect of the invention, there is provided an extract of a plant or plants from the Mesembryanthemaceae family, such as *Mesembryanthemum tortuosum*, having an alkaloid profile comprising at least 20%, or at least 50%, or at least 70% (w/w) Δ7 mesembrenone.

According to a preferred embodiment of this aspect of the invention, the alkaloid profile comprises at least 70% (w/w) Δ7 mesembrenone. Preferably the majority of the balance of the alkaloids is mesembrine and mesembrenone.

In one form of this aspect of the invention the extract has an alkaloid profile comprising at least about 70% (w/w) Δ7 mesembrenone, about 20% (w/w) mesembrine and about 10% (w/w) mesembrenone.

The total alkaloid content of the extract is typically at least 10%, or at least 15%, or at least 20% thereof.

According to a second aspect of the invention, there is provided a method of treating cancer comprising administering to a patient in need of such treatment a therapeutically effective amount of an extract of a plant or plants from the Mesembryanthemaceae family, such as *Mesembryanthemum tortuosum*, having an alkaloid profile comprising at least 20%, or at least 50%, or at least 70% (w/w) Δ7 mesembrenone.

According to a third aspect of the invention, there is provided an extract of a plant or plants from the Mesembryanthemaceae family, such as *Mesembryanthemum tortuosum*, having an alkaloid profile comprising at least 20%, or at least 50%, or at least 70% (w/w) Δ7 mesembrenone for use in a method of treating cancer in a patient in need of such treatment.

According a fourth aspect of the invention, there is provided a composition comprising an alkaloid content/profile as hereinbefore defined.

According to a fifth aspect of the invention, there is provided an anti-cancer composition comprising Δ7 mesembrenone, mesembrenone, or a combination of Δ7 mesembrenone and mesembrenone.

In a preferred embodiment of this aspect of the invention, the anti-cancer composition is a pharmaceutical composition comprising Δ7 mesembrenone and a pharmaceutically acceptable carrier, together with other optional pharmaceutically acceptable excipients.

In a particularly preferred embodiment of this aspect of the invention, the pharmaceutical composition comprises at least 80% pure, more preferably at least 90% pure, isolated Δ7 mesembrenone.

According to a fifth aspect of the invention, there is provided a method of treating cancer comprising administering to a patient in need of such treatment a therapeutically effective amount of Δ7 mesembrenone, mesembrenone, or a combination of Δ7 mesembrenone and mesembrenone.

In a preferred embodiment of this aspect of the invention, a therapeutically effective amount of Δ7 mesembrenone is administered to a patient in need of such treatment.

The Δ7 mesembrenone is preferably at least 80% pure, more preferably at least 90% pure, isolated Δ7 mesembrenone.

According to a sixth aspect of the invention, there is provided an anti-cancer composition comprising as active ingredient Δ7 mesembrenone, mesembrenone, or a combination of Δ7 mesembrenone and mesembrenone for use in a method of treating cancer in a patient in need of such treatment.

In a preferred embodiment of this aspect of the invention, the anti-cancer composition is a pharmaceutical composition comprising Δ7 mesembrenone and a pharmaceutically acceptable carrier, together with other optional pharmaceutically acceptable excipients.

In a particularly preferred embodiment of this aspect of the invention, the pharmaceutical composition comprises at least 80% pure, more preferably at least 90% pure, isolated Δ7 mesembrenone.

In the case of pharmaceutical compositions, in some embodiments of the invention, they are provided in unit dosage form, each unit dose comprising from about 5mg to about 70mg, or from about 10mg to about 65mg, or from about 15mg to about 60mg Δ7 mesembrenone.

In some embodiments of the invention, each unit dose comprises from about 1.5mg to about 20mg, or from about 3mg to about 18.5mg, or from about 4mg to about 17.5mg mesembrine.

In some embodiments of the invention, each unit dose comprises from about 0.75mg to about 10mg, or from about 1.5mg to about 9.5mg, or from about 2mg to about 9mg mesembrenone.

In some embodiments of the invention, the disease or condition responsive to treatment with an anticancer agent is with specific cytotoxicity on breast epithelial carcinoma cells (MCF-7).

In some embodiments of the invention, the cancer treated by the extracts, compositions and isolated actives (isolates) of the invention is breast cancer.

BRIEF DESCRIPTION OF THE FIGURES

The invention will now be discussed in more detail, by way of example only, with reference to the accompanying figures in which.

DESCRIPTION OF PREFERRED EMBODIMENTS

Figure 1:
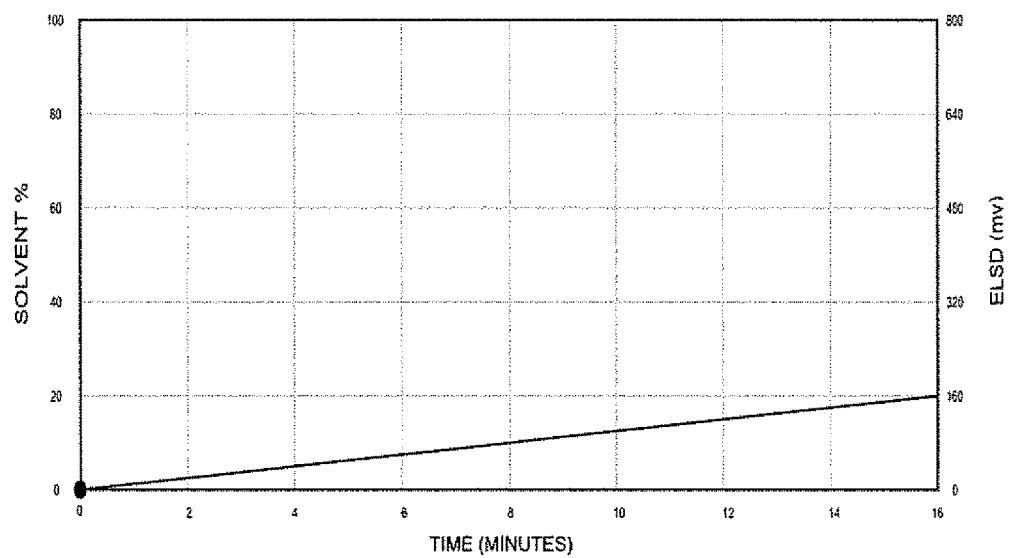
FIG. 1 is an MPLC solvent gradient graph of extraction of actives from *Sceletium tortuosum;*

Anti-cancer compositions of the invention comprise active ingredients derived from extracts of a plant or plants from the Mesembryanthemaceae family, such as *Mesembryanthemum tortuosum*, in particular of the DV-17 variety or isolated actives or combinations of isolated actives derived from the extracts.

"The DV-17 variety" is a unique variety of *Mesembryanthemum (Sceletium) tortuosum* selectively propagated for its high alkaloid content, recognizable profile and vigorous growth. Chemical analysis shows a distinctive fingerprint to the levels of mesembrine, mesembrenone, $\Delta 7$ mesembrenone and epimesembranol as well as other active and related compounds pre-fermentation.

Examples below are of 2 commercially available *Mesembryanthemum* plants showing distinct alkaloid profiles compared to the DV-17 variety.

Yield figures for mesembrine are typically between 12 mg and 15 mg per gram of dried DV-17 whole herba.

| Sample ref | $\Delta 7$ mesembrenone % | Mesembrenone % | Mesembranol % | Mesembrine % |
|---|---|---|---|---|
| DV-8 |  | 40.2 | 3.8 | 56.0 |
| DV-12 |  | 45.8 | Trace | 54.2 |
| DV-17 | <10 | ≤20 | Trace | >70 |

The composition that comprises an extract of a plant or plants from the Mesembryanthemaceae family, such as *Mesembryanthemum tortuosum*, as active ingredient typically has an alkaloid profile comprising at least 20% or at least 50% or at least 70% $\Delta 7$ mesembrenone. It preferably comprises at least 70% $\Delta 7$ mesembrenone, about 20% mesembrine and about 10% mesembrenone.

In preferred embodiments of the invention the anti-cancer composition comprises $\Delta 7$ mesembrenone, mesembrenone or a combination of $\Delta 7$ mesembrenone and mesembrenone. In particularly preferred embodiments of the invention, the composition comprises $\Delta 7$ mesembrenone.

The compositions of the invention may be formulated in any suitable form for pharmaceutical administration, such as for example tablets, capsules and as suppositories. The formulations may be designed for use orally and transdermally via the rectum.

The pharmaceutical composition of the invention may comprise a hydro-methanolic extract of the plant containing desired amounts of $\Delta 7$ mesembrenone, mesembrine and mesembrenone. Accordingly, the pharmaceutical compositions, whilst derived from a natural plant material, contain a known and specified content of the active components.

Plant Extract

Plant (*Mesembryanthemum tortuosum* DV-17 variety) is harvested and dried (NMT8% moisture) then milled to 250 micron. 2 kg of said plant material is added to 10 liters of methanol (82% hydro-methanolic) at 35° C. with the pH adjusted to 2.4 with hydrochloric acid then allowed to stir for 24 hrs. The crude solvent extract is removed by pressing before an additional 2 liters of methanol 88% is again added to the plant material—this time without the addition of acid—and stirred for 9 hrs before repressing.

The combined crude extract (9.8 liters) is filtered thrice through polypropylene membranes—1st 100 μm, 2nd 40 μm, and 3rd 5 μm.

7.8 liters of the main solvent (methanol) is recovered under reduced pressure—318 mb at 40° C.

The high recovery of mesembrine at this stage allows for easy oxidation to $\Delta 7$ mesembrenone; as would be evident to those skilled in the art; to increase $\Delta 7$ mesembrenone to the desired level. By way of example, the following oxidation method reported by Peter W. Jeffs (THE ALKALOIDS, Chemistry and Physiology, Volume XIX, page 55) may be used.

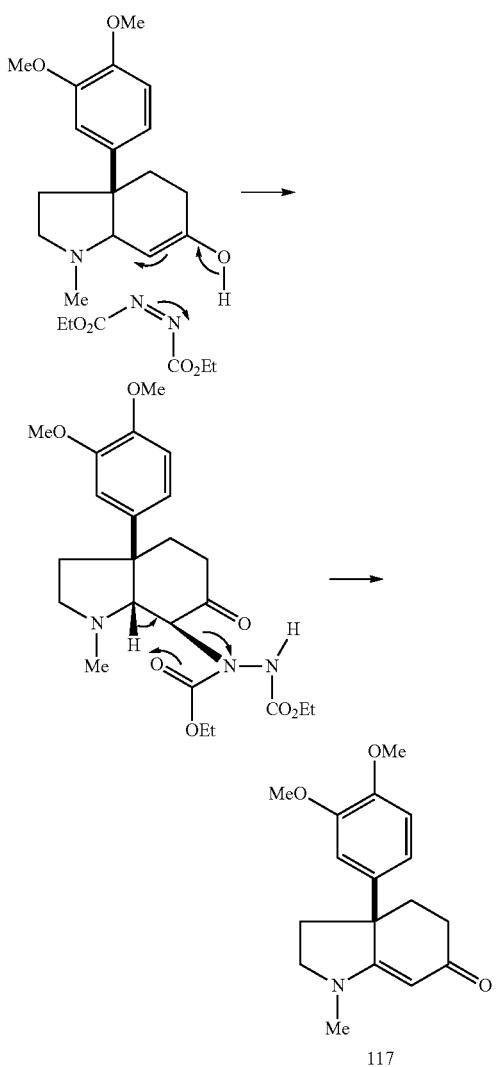

The combined aqueous phase is basified to pH 7.7 with a 25% ammonia solution and then extracted 4× with 500 mL SCM.

All organic phases are pooled and washed once with brine. After phase separation on standing the bottom organic layer is tapped off and dried with anhydrous sodium sulphate.

The solvent is removed completely under vacuum leaving a crude *Sceletium* extract. In order to obtain a refined extract or composition comprising at least 70% Δ7 mesembrenone, further isolation of actives was undertaken to confine the extract to the active anti-cancer agents.

Isolation of Actives

The column is loaded onto a MPLC (Grace, Reveleris) instrument, set and run as follows:

Cartridge: Grace Reveleris 80 g Silica Cartridge
Equilibration: 3 CV
Flow rate: 47 mL/min
UV threshold: 0.03 AU
UV1 wavelength: 228 nm
UV2 wavelength: 288 nm
ELS© threshold: 5 mv
ELSD carrier: Iso-proponal
Set peaks: Collect peaks
Injection type: Manual (5 g)
Solvent A: DCM
Solvent B: Methanol
Mobile phase: A:B
Run time: 16 min As reflected in FIG. 1 of the accompanying figures, the eluting solvent gradient is gradually changed from 0% Methanol to 20% Methanol over 16 min.

Combine fractions of interest as confirmed by TLC-Evaporate solvent under reduced pressure to obtain the purified alkaloid fractions of mesembrenone, mesembrine and Δ7 mesembrenone.

Drying Product

Combine the following in a suitable container: 25 g alkaloid containing composition dissolved in 150 mLs of 20% Ethanol Adjust pH to 5.1 with concentrated hydrochloric acid.

Add 75 g Dridex (DE9) to the alkaloid solution under high sheer conditions until homogenized and then place paste in a freeze dryer overnight.

Product is then reduced to a fine free flowing powder using a colloidal mill or laboratory hammer mill.

Yield: 100 g (actual 98.7 g)
Product Characteristics: Free flowing powder
Colour: Tan
Practical Size: <75 μm
Moisture Content: <3%
Total Alkaloids: NLT 21% w/w
Alkaloid Profile: 68-70% of Δ7 mesembrenone HCL Thin-Layer Chromatography For qualitative screening purposes the following system is suitable: AnalTech, Inc RPS-F Silica Gel W/UV254 (250 μm layer thickness) and developed in water/methanol/ammonia solution (N7), in methanol (18:6:0.5). The plates are dried at 60° C. for 10 minutes, studied under UV254 and UV365 and then sprayed with Dragendorffs spray reagent.

(Rf of Δ7 mesembrenone=0.82)

High Performance Liquid Chromatography (HPLC)

The alkaloids of the invention may directly be extracted in ethanol, methanol or any other suitable solvent (see, for example, http://www.ncbi.nlm.nih.gov/pubmed/21486531). For HPLC the sample has to be filtered (e.g. 0.45 μm filter) in order to protect the columns from impurities.

Separation of the stabilized extract using a mobile phase comprising of water:acetonitrile:ammonium hydroxide solution mixed in a ratio of 70:30:0.01 (v:v:v).

Column-Hypersil® 150×4.6 mm i.d, C18 column (Phenomenex®, Torrence, Calif., USA).

Figure 2:
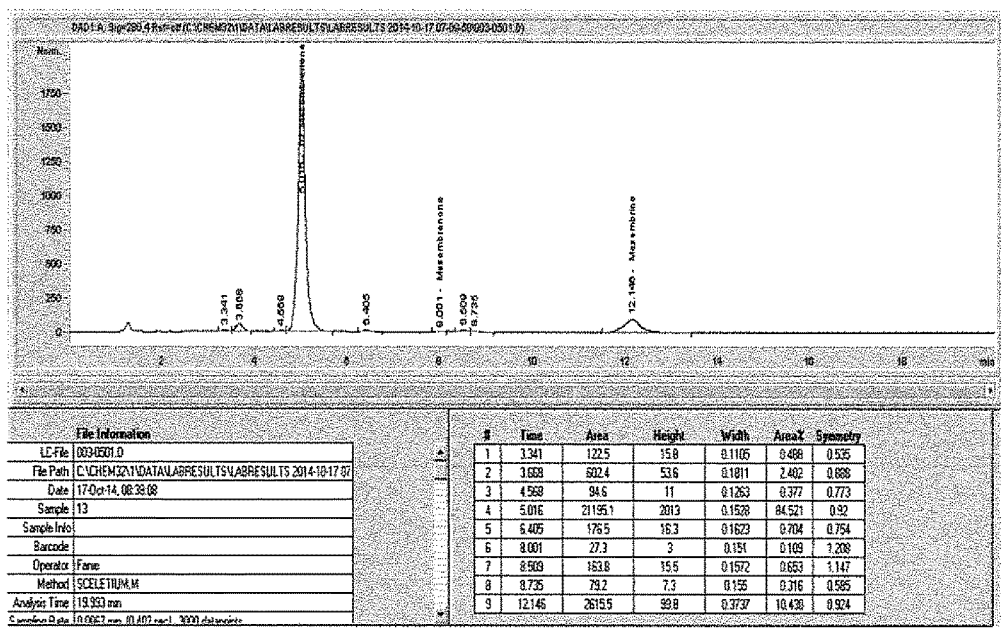
FIG. 2 is a HPLC chromatograph of an extract of the invention comprising >70% of Δ7 mesembrenone.

The results of the HPLC extraction are depicted in FIG. 2 of the accompanying figures.

Evaluation of the Effect of an Extract and Isolates from an Extract of *Sceletium tortuosum* on Normal and Cancerous Breast Epithelial Cells In a preliminary test, the effect of an extract of *Sceletium tortuosum* (hereinafter PNP50) on the viability of normal and cancerous breast epithelial cells in culture was investigated.

Briefly, the procedure entailed 24 hour treatment of normal breast epithelial cells (MCF-12A) and breast epithelial carcinoma cells (MCF-7) with varying doses of the *Sceletium* extract named PNP50 (ranging from 0.25 to 1.5 mg/ml). At the end of this period, the mitochondrial viability of cells was assessed using the micro culture tetrazolium (MTT) assay method. Viability was measured and expressed relative to an appropriate control.

Figure 3:
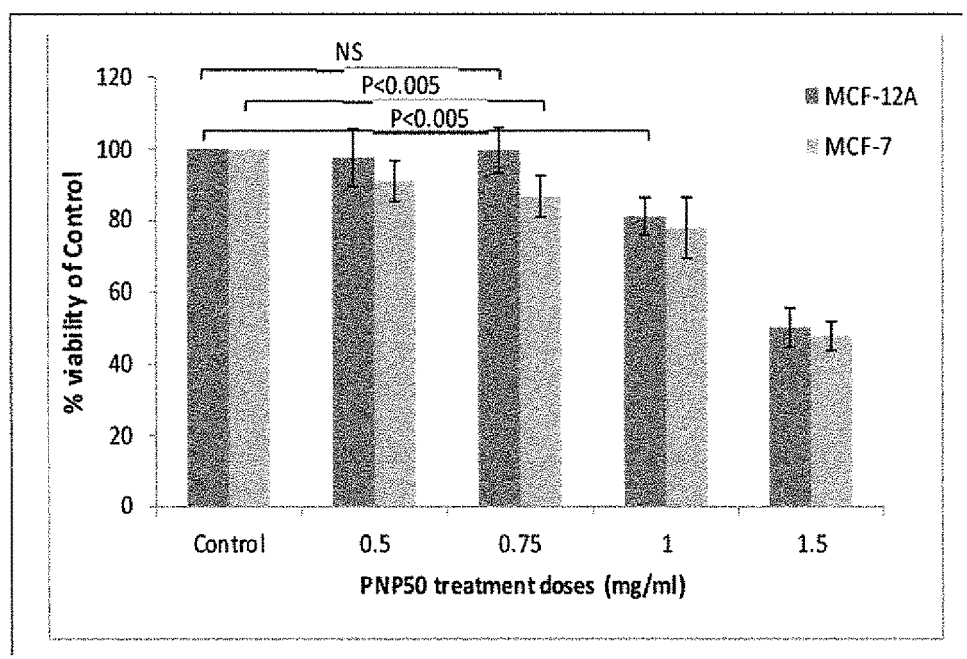
FIG. 3 is a bar graph depicting the results of the effect of an extract (PNP50) of *Sceletium tortuosum* showing the viability thereof on normal and cancerous breast epithelial cells.

Results are illustrated in FIG. 3 of the accompanying figures and are expressed as the percentage of cells still viable after 24 hours. Bars are means of repeated experiments (a minimum of 5 repeats) and error bars indicate standard deviations. (For clarity, only statistical results relative to interpretation and conclusion are presented graphically.)

As is evident from the graph depicted in FIG. 3, extract PNP50 had no adverse effect on cell viability of normal breast epithelial cells at doses below 1 mg/ml, but became toxic to normal cells at a dose of 1 mg/ml, with increasing toxicity at higher doses. Carcinoma cells exhibited higher vulnerability to the extract when compared to normal cells, so that only 0.75 mg/ml was sufficient to decrease cell viability significantly.

As the results point to a positive effect of the tested extract as an anti-cancer modality, provided it is administered at the appropriate concentrations, further tests were conducted on specific candidates of the extracts on their effect on viability of normal and cancerous breast epithelial cells in culture.

Further investigations were conducted on isolates from the plant extracts, most notably Δ7 mesembrenone and mesembrenone, which were evaluated against an unknown non-alkaloid isolate from the extract. To calculate doses, the concentrations of the specific components for serving sizes of 15 mg, 30 mg and 60 mg per person per day for Δ7 mesembrenone, mesembrenone and non-alkaloids respectively were expressed as a fraction of total body fluid volume. In an attempt to account for digestive losses, these concentrations were halved, to reach cell-culture "equivalent" doses of 0.5 ug/ml, 1 ug/ml and 2 ug/ml respectively. Following standard laboratory practice, a range of doses around these was assessed. For clarity, only 3 concentrations per component are presented (doses of 10-fold smaller were also tested for all components, but were not different from lowest doses presented herein and thus omitted).

Briefly, the procedure itself entailed 24-hour treatment of confluent cell culture samples of normal breast epithelial cells (MCF-12A) and breast epithelial carcinoma cells (MCF-7) with varying doses of the test products. At the end of this period, the mitochondrial viability of cells was assessed using the XTT assay method. Viability was measured and expressed relative to an appropriate control.

Figure 4:
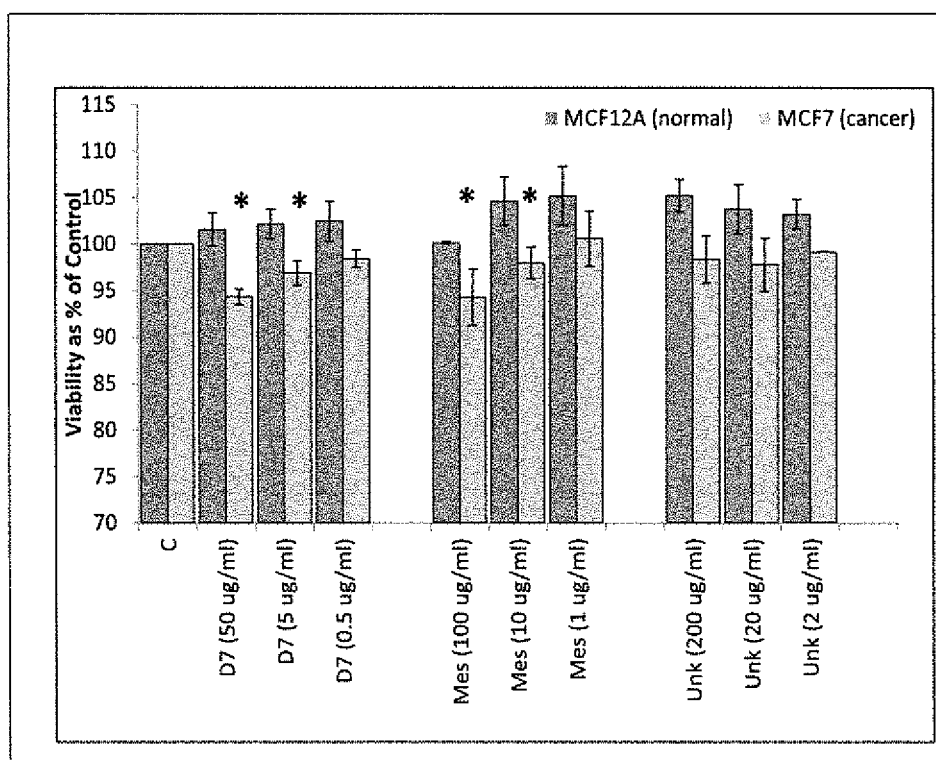
FIG. 4 is a bar graph depicting the results of the effect of isolates extracted from *Sceletium tortuosum* showing the viability thereof on normal and cancerous breast epithelial cells.

Results are illustrated in FIG. 4 of the accompanying drawings. Results are expressed as the percentage of viable cells after a 24 hour incubation with the test substances. Bars are means of repeated experiments (a minimum of 3 repeat experiments in triplicate) and error bars indicate standard deviations from the mean. Asterisk (*) indicate significant reductions in cancer cell viability.

Both Δ7 mesembrenone and mesembrenone showed clear dose-response effects on viability of cancer cells. Δ7 mesembrenone, which was administered at a dose 50% less than mesembrenone, appears to provide the most potent anti-cancer effect, while not affecting normal cell survival, even at the highest dose assessed. Mesembrenone also decreased survival of cancer cells, although the highest dose seemed to limit growth of normal cells to some extent as well. In terms of the unknown non-alkaloid fraction, none of the doses decreased cancer cell viability in comparison to control levels and certainly no dose-effect was evident.

Those skilled in the art will recognize that the strength of this anti-cancer effect is a rare occurrence—high effectivity with no adverse effects to normal cells. Given the promising results obtained for Δ7 mesembrenone and mesembrenone in this model, which is an estrogen-sensitive model, it is intended that the study will be followed up by an in vivo assessment using a rodent cancer model, as well as expansion of the investigation to a non-estrogen-sensitive model, such as colon cancer.

By way of non-limiting example only, pharmaceutical compositions of the invention are illustrated in the following examples.

EXAMPLE 1

A pharmaceutical strength oral capsule containing 102 mg of a composition of the invention—equal to 15 mg Δ7 mesembrenone, 4.29 mg mesembrine, 2.14 mg mesembrenone—and conventional pharmaceutical excipients

| | |
|---|---|
| Malto-dextrin (DE9) | 510 mg |
| Δ7 composition | 102 mg |
| Nu-FLOW ® (Rice concentrate) | 8.0 mg |
| Nu-Rice ® (Rice extract) | 0.5 mg |

A typical dose of the oral tablet composition is from 1 to 4 inclusive daily under the supervision of a medical practitioner.

EXAMPLE 2

A pharmaceutical strength oral capsule containing 15 mg Δ7 mesembrenone and conventional pharmaceutical excipients

| | |
|---|---|
| Malto-dextrin (DE9) | 597 mg |
| Δ7 mesembrenone (isolate) | 15 mg |
| Nu-FLOW ® (Rice concentrate) | 8.0 mg |
| Nu-Rice ® (Rice extract) | 0.5 mg |

A typical dose of the oral tablet composition is from 1 to 4 inclusive daily under the strict supervision of a medical practitioner.

EXAMPLE 3

Suppository formulation, formulated as disclosed in U.S. Pat. No. 2,538,127 A, containing 15 mg Δ7 mesembrenone, 4.29 mg mesembrine, 2.14 mg mesembrenone.

A typical dose of the composition is from 1 to 4 inclusive daily under the strict supervision of a medical practitioner.

The invention claimed is:

1. An anti-cancer composition derived from an extract of a plant from the Mesembryanthemaceae family, the anti-cancer composition comprising Δ7 mesembrenone, and one or more of mesembrine and mesembrenone, wherein with respect to the Δ7 mesembrenone and the one or more of mesembrine and mesembrenone in the composition there is at least 50% (w/w) Δ7 mesembrenone, wherein the composition is in the form of a tablet, capsule, or suppository.

2. The composition of claim 1, wherein the plant is *Mesembryanthemum tortuosum*.

3. The composition of claim 1, wherein with respect to the Δ7 mesembrenone and the one or more of mesembrine and mesembrenone, the composition consists essentially of about 68-70% (w/w) Δ7 mesembrenone, about 20% (w/w) mesembrine and about 10% (w/w) mesembrenone.

4. The composition of claim 1, wherein the Δ7 mesembrenone and the one or more of mesembrine and mesembrenone, together comprise at least 10% of the composition.

5. The anti-cancer composition of claim 1, wherein the Δ7 mesembrenone has a purity of at least 80%.

6. The anti-cancer composition of claim 1, having specific cytotoxicity on breast epithelial carcinoma cells (MCF-7).

7. A method of treating cancer comprising administering to a patient in need of such treatment a therapeutically effective amount of the anti-cancer composition of claim 1.

8. The method of claim 7, wherein the cancer is breast cancer.

9. A unit dosage form comprising:
   about 5 mg to about 70 mg of Δ7 mesembrenone; and either or both of 1.5 mg to about 20 mg mesembrine; and
   0.75 mg to about 10 mg mesembrenone,
   wherein the unit dosage form is in the form of a tablet, capsule, or suppository.

10. The composition of claim 1 comprising at least about 70% (w/w) Δ7 mesembrenone.

11. The composition of claim 1, wherein the Δ7 mesembrenone and the one or more of mesembrine and mesembrenone, together comprise at least 20% of the composition.

12. The unit dosage form of claim 9, comprising:
   about 10 mg to about 65 mg of Δ7 mesembrenone; and either or both of 3 mg to about 18.5 mg mesembrine; and
   1.5 mg to about 9.5 mg mesembrenone.

13. The unit dosage form of claim 9, comprising:
   about 15 mg to about 60 mg of Δ7 mesembrenone; and either or both of 4 mg to about 17.5 mg mesembrine; and
   2 mg to about 9 mg mesembrenone.

* * * * *